US011331086B2

(12) United States Patent
Bang et al.

(10) Patent No.: US 11,331,086 B2
(45) Date of Patent: May 17, 2022

(54) BIOPSY APPARATUS AND METHOD FOR OPERATING THE SAME

(71) Applicant: Samsung Medison Co., Ltd., Gangwon-do (KR)

(72) Inventors: Won-chul Bang, Gyeonggi-do (KR); Young-taek Oh, Gyeonggi-do (KR); Ji-won Ryu, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 188 days.

(21) Appl. No.: 15/795,566

(22) Filed: Oct. 27, 2017

(65) Prior Publication Data

US 2018/0116643 A1 May 3, 2018

(30) Foreign Application Priority Data

Oct. 28, 2016 (KR) ........................ 10-2016-0142147

(51) Int. Cl.
*A61B 10/02* (2006.01)
*A61B 8/08* (2006.01)
(Continued)

(52) U.S. Cl.
CPC ............ *A61B 10/0233* (2013.01); *A61B 8/08* (2013.01); *A61B 8/0841* (2013.01); *A61B 8/4254* (2013.01); *A61B 8/4416* (2013.01); *A61B 8/085* (2013.01); *A61B 8/0825* (2013.01); *A61B 8/4405* (2013.01); *A61B 8/4427* (2013.01);
(Continued)

(58) Field of Classification Search
CPC . A61B 10/0233; A61B 8/0841; A61B 8/4254; A61B 8/0825; A61B 8/085; A61B 2010/0208; A61B 2017/3413
See application file for complete search history.

(56) References Cited

U.S. PATENT DOCUMENTS 8,369,592 B2  2/2013  Leroy et al.
8,447,384 B2  5/2013  Xu et al.
(Continued)

FOREIGN PATENT DOCUMENTS

JP  2013-118998 A  6/2013
JP  2015-136494 A  7/2015
(Continued)

OTHER PUBLICATIONS

Korean Notice of Allowance dated Sep. 27, 2018 issued in Korean Patent Application No. 10-2016-0142147 (with English translation).
(Continued)

*Primary Examiner* — Catherine B Kuhlman
*Assistant Examiner* — Sean A Frith
(74) *Attorney, Agent, or Firm* — Morgan, Lewis & Bockius LLP (57) ABSTRACT

Provided is a biopsy apparatus including an ultrasound probe; a biopsy needle located at a side of the ultrasound probe and including an electromagnetic (EM) sensor; a tracker configured to obtain position and movement direction information of the biopsy needle; and a controller configured to receive, from the tracker, the position and movement direction information of the biopsy needle, and to determine an operation mode, based on the position and movement direction information.

7 Claims, 7 Drawing Sheets

(51) Int. Cl.
*A61B 8/00* (2006.01)
*A61B 17/34* (2006.01)

(52) U.S. Cl.
CPC ....... *A61B 8/467* (2013.01); *A61B 2010/0208* (2013.01); *A61B 2017/3413* (2013.01)

(56) References Cited

U.S. PATENT DOCUMENTS

| | | | |
|---|---|---|---|
| 8,708,912 B2 | 4/2014 | Osaka et al. | |
| 9,468,413 B2 * | 10/2016 | Hall | A61B 6/12 |
| 2007/0232882 A1 * | 10/2007 | Glossop | A61B 8/0841 |
| | | | 600/407 |
| 2008/0009724 A1 | 1/2008 | Lee et al. | |
| 2008/0091106 A1 | 4/2008 | Kim et al. | |
| 2010/0081920 A1 | 4/2010 | Whitmore, III et al. | |
| 2012/0046521 A1 * | 2/2012 | Hunter | A61B 1/2676 |
| | | | 600/104 |
| 2012/0071749 A1 | 3/2012 | Xu et al. | |
| 2012/0190982 A1 | 7/2012 | Hyoun et al. | |
| 2013/0324841 A1 | 12/2013 | Kamen et al. | |
| 2015/0201906 A1 * | 7/2015 | Yoshida | A61B 8/5207 |
| | | | 600/424 |
| 2016/0018520 A1 * | 1/2016 | Hirai | A61B 8/5261 |
| | | | 367/11 |
| 2016/0081653 A1 * | 3/2016 | Masuda | A61B 8/0841 |
| | | | 600/424 |
| 2016/0151039 A1 * | 6/2016 | Morikawa | A61B 8/06 |
| | | | 600/424 |
| 2016/0174934 A1 * | 6/2016 | Cong | A61B 8/08 |
| | | | 600/459 |
| 2016/0242855 A1 * | 8/2016 | Fichtinger | A61B 17/320016 |
| 2016/0302871 A1 * | 10/2016 | Gregerson | A61B 34/20 |
| 2016/0317118 A1 * | 11/2016 | Parthasarathy | G06K 9/4614 |

FOREIGN PATENT DOCUMENTS

| | | |
|---|---|---|
| JP | 2015-139576 A | 8/2015 |
| KR | 10-2007-0110965 A | 11/2007 |
| KR | 10-2008-0034664 A | 4/2008 |
| KR | 10-2012-0085680 A | 8/2012 |
| KR | 10-2012-0093603 A | 8/2012 |
| KR | 10-2016-0089687 A | 7/2016 |
| WO | 2006/054635 A1 | 5/2006 |
| WO | 2009/153723 A1 | 12/2009 |
| WO | WO-2009153723 A1 * 12/2009 ........... A61B 8/4254 |
| WO | WO-2010132985 A1 * 11/2010 ........... A61B 8/0833 |
| WO | 2013-085139 A1 | 6/2013 |
| WO | 2013/111133 A1 | 8/2013 |
| WO | 2015-116469 A1 | 8/2015 |

OTHER PUBLICATIONS

European Search Report dated Mar. 21, 2018.
Korean Search Report dated Feb. 28, 2018.

* cited by examiner

BIOPSY APPARATUS AND METHOD FOR OPERATING THE SAME

CLAIM OF PRIORITY

This application claims the benefit of Korean Patent Application No. 10-2016-0142147, filed on Oct. 28, 2016, in the Korean Intellectual Property Office, the disclosure of which is incorporated herein in its entirety by reference.

BACKGROUND

1. Field

The present disclosure generally relates to a biopsy apparatus and a method of operating the biopsy apparatus. More particularly, the present disclosure relates to an apparatus including a biopsy needle attached to an ultrasound probe and a method of registering and correcting ultrasound images and images of other modalities.

2. Description of the Related Art

In general, a typical ultrasound diagnosis apparatus known in the art transmits an ultrasound signal generated by a transducer of an ultrasound probe to a subject for diagnosis, such as a human body, and may receive a signal reflected from the subject. After processing the received signal, the ultrasound diagnosis apparatus can generate images of a region (e.g., soft tissue or blood stream) inside the subject.

These ultrasound diagnosis apparatuses may also take biopsies by inserting a medical needle such as a biopsy needle into a lesion region of the subject body. While the biopsy operation is underway, the medical technician or operator may use the ultrasound features of the apparatus to observe the inside of the subject's body. The biopsy feature may be used to diagnose cancer or other diseases. In general, tumors or inflammatory masses may grow on various organs such as livers, kidneys, pancreases, breasts, etc., and biopsies may be utilized in order to distinguish a malignant tumor requiring surgery or administration of anticancer drugs from a benign tumor or an inflammatory mass.

However, it is often difficult to precisely recognize the position or direction of the biopsy needle when the biopsy needle is inserted into the subject's body. Advancements in the art have been made where the biopsy needle includes a position tracking sensor. However, in order to attach the biopsy needle including a position tracking sensor to the ultrasound probe, the ultrasound probe need to be redesigned to have a groove such that a bracket or a guide jig can be mounted in the body of the ultrasound probe.

SUMMARY

Provided are a biopsy apparatus that includes a biopsy needle which includes a sensor, and a method of operating the biopsy apparatus for registering an ultrasound image and an image of another modality and performing a biopsy function, whereby the structure of the body of the ultrasound probe need not be changed.

Additional aspects will be set forth in part in the description which follows and, in part, will be apparent from the description, or may be learned by practice of the presented embodiments.

According to an aspect of an embodiment, a biopsy apparatus includes an ultrasound probe configured to transmit an ultrasound signal to an object and to receive an echo signal reflected from the object, to thereby obtain an ultrasound image; a biopsy needle located at a side of the ultrasound probe, and including an electromagnetic (EM) sensor; a tracker configured to obtain position and movement direction information of the biopsy needle; and a controller configured to receive, from the tracker, the position and movement direction information of the biopsy needle, and to determine an operation mode based on the position and movement direction information, wherein the operation mode is selected from an image registration mode where image registration is performed between the ultrasound image and an image of another modality, and a biopsy mode where a biopsy is performed using the biopsy needle.

According to an aspect of another embodiment, a method includes obtaining position and movement direction information of the biopsy needle using an electromagnetic (EM) sensor included in the biopsy needle; determining an operation mode based on the position and movement direction information, wherein the operation mode is selected from an image registration mode where image registration is performed between an ultrasound image and an image of another modality, and a biopsy mode where a biopsy is performed using the biopsy needle; and when the operation mode is the biopsy mode, correcting the image of another modality for registration with the ultrasound image.

According to an aspect of another embodiment, a computer-readable recording medium includes a program for implementing the above method using a computer.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

The present specification describes principles of the present disclosure and sets forth embodiments thereof to clarify the scope of the present disclosure and to allow those of ordinary skill in the art to implement the embodiments. The disclosed embodiments are exemplary and not limiting.

In the present specification, "image" may refer medical images obtained by a medical imaging apparatus such as an ultrasound imaging apparatus, a magnetic resonance imaging (MRI) apparatus, a computed tomography (CT) apparatus, an X-ray apparatus, or the like.

Furthermore, in the present specification, "object" may be a target to be imaged such as a human body, an animal body, or a part of the human or animal. For example, the object may be a body part (such as an organ) or a phantom.

Throughout the specification, "ultrasound image" may refer to images of an object generated from ultrasound signals transmitted to the object and ultrasound echo signals reflected from the object.

Throughout the specification, "registration" may refer to the process of one-to-one matching medical images of different modalities.

As used herein, the term "and/or" includes any and all combinations of one or more of the associated listed items. Expressions such as "at least one of," when preceding a list of elements, modify the entire list of elements and do not modify the individual elements of the list.

Figure 1:
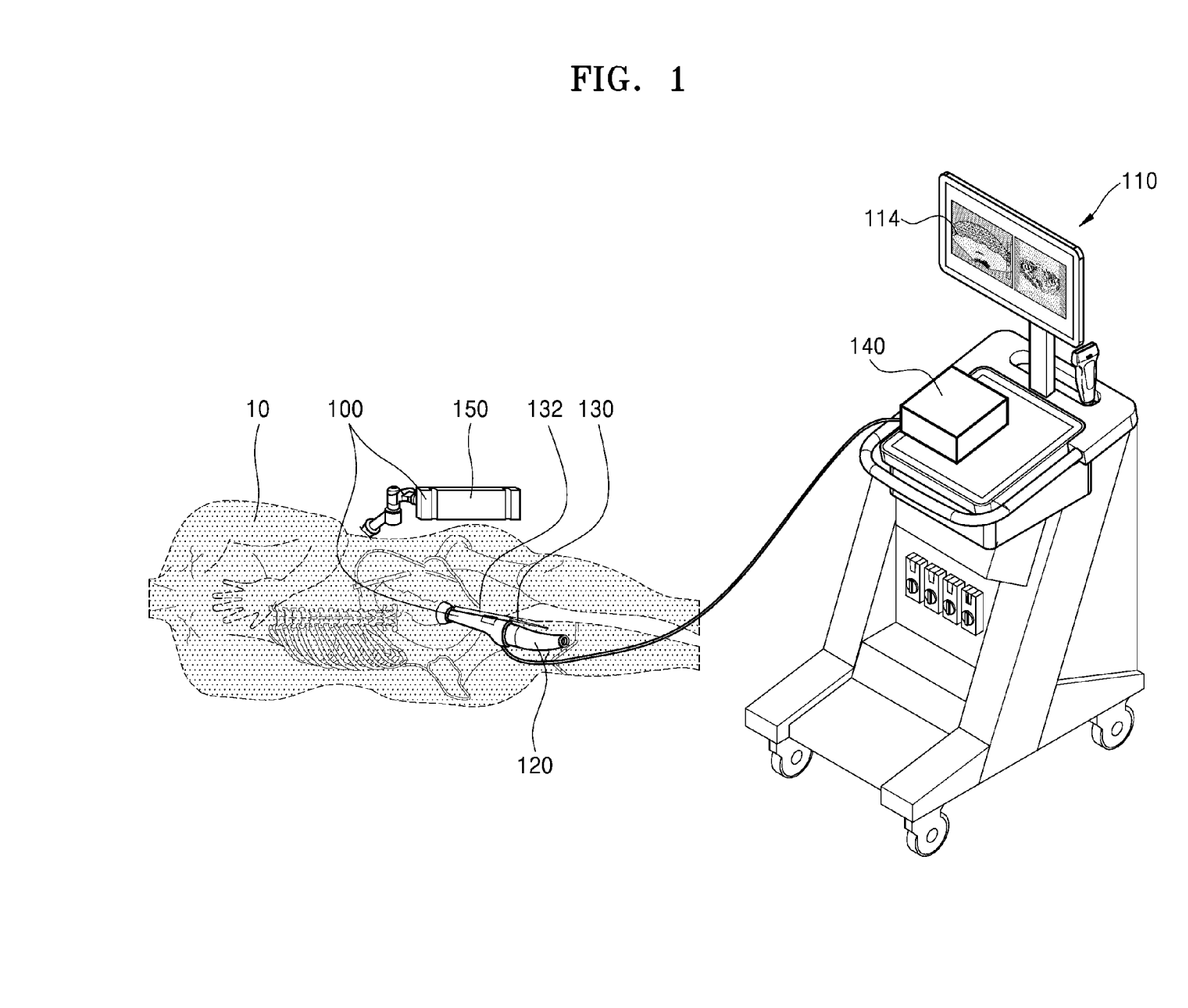
FIG. 1 is a schematic diagram illustrating a biopsy apparatus and a method of operating the biopsy apparatus, according to an embodiment.

FIG. 1 is a schematic diagram illustrating a biopsy apparatus 100 and a method of operating the biopsy apparatus 100, according to an embodiment.

The biopsy apparatus 100 may be a medical apparatus for obtaining ultrasound images of the object 10, and for performing biopsies and medical treatments.

Referring to FIG. 1, the biopsy apparatus 100 may include an ultrasound imaging apparatus 110, an ultrasound probe 120, a biopsy needle 130, a guide cover 132, a tracker 140, and an electromagnetic field generator 150.

The ultrasound probe 120 may transmit an ultrasound signal to the object 10, and may receive an ultrasound echo signal reflected from the object 10. Referring to FIG. 1, the ultrasound probe 120 is connected to the ultrasound imaging apparatus 110 via a wire, but the present disclosure is so limited. For example, the ultrasound probe 120 may be wirelessly connected to the ultrasound imaging apparatus 110.

The ultrasound imaging apparatus 110 may receive the ultrasound echo signal from the ultrasound probe 120, and may perform image-processing on the ultrasound echo signal to generate ultrasound images of a region inside the object 10. The ultrasound imaging apparatus 110 may include a display 114 to display the ultrasound images.

The biopsy needle 130 may be a medical needle that is inserted into a lesion region of the object 10 through a hole in the object body. The biopsy needle 130 may Clear Track™ or Virtual Track™ needles.

The biopsy needle 130 may be located at one side of the ultrasound probe 120. In the present embodiment, the biopsy needle 130 may be located in the guide cover 132 attached to one side of the ultrasound probe 120. The biopsy needle 130 may be enveloped by the guide cover 132 and may be movable in first and second directions in the guide cover 132. The biopsy needle 130 enveloped by the guide cover 132 may be inserted toward the inside of the object 10

The electromagnetic field generator 150 may be located near the ultrasound probe 120 and the biopsy needle 130, and may generate an electromagnetic field within a preset range. The electromagnetic field generated by the electromagnetic field generator 150 can be used to detect the positions of the ultrasound probe 120 and the biopsy needle 130 in a three-dimensional (3D) coordinates system.

Accordingly, in the present embodiment, the biopsy needle 130 may include an electromagnetic sensor (EM sensor) to detect the electromagnetic field.

The tracker 140 may obtain position and movement direction information regarding the biopsy needle 130 when it is inserted into the object 10 for biopsy. The tracker 140 may track the movement direction of the biopsy needle 130 using the EM sensor and record the movement direction as a direction vector in a 3D coordinates system.

The ultrasound imaging apparatus 110 may receive the position and movement direction information regarding the biopsy needle 130 from the tracker 140. In turn, the ultrasound imaging apparatus 110 may determine an operation mode based on the received position and movement direction information. In the present embodiment, the operation modes may include an image registration mode where ultrasound images are registered with images of other modalities, and a biopsy mode using the biopsy needle 130.

When the ultrasound imaging apparatus 110 is the biopsy mode, the ultrasound imaging apparatus 110 may pause images of other modalities so that the images of other modalities can be properly registered with the ultrasound images. The image may include, but is not limited to, at least one of a CT image, an MRI image, and an X-ray image.

When the biopsy needle 130 is moved inside the object 10 during the biopsy mode, the ultrasound imaging apparatus 110 may pause the images of other modalities so that they can be properly registered with the ultrasound images.

In order to attach the biopsy needle 130 including a position tracking sensor such as the EM sensor to the ultrasound probe 120, it is required to re-design the ultrasound probe 120 by making a groove for attaching a member such as a bracket to the body of the ultrasound probe 120. The biopsy apparatus 100 according to the embodiment of FIG. 1 may perform both image registration and biopsy by using the biopsy needle 130 with an EM sensor. Thus, there is no need to re-design the ultrasound probe 120 and therefore the design and manufacturing costs of the biopsy apparatus may be reduced.

Figure 2:
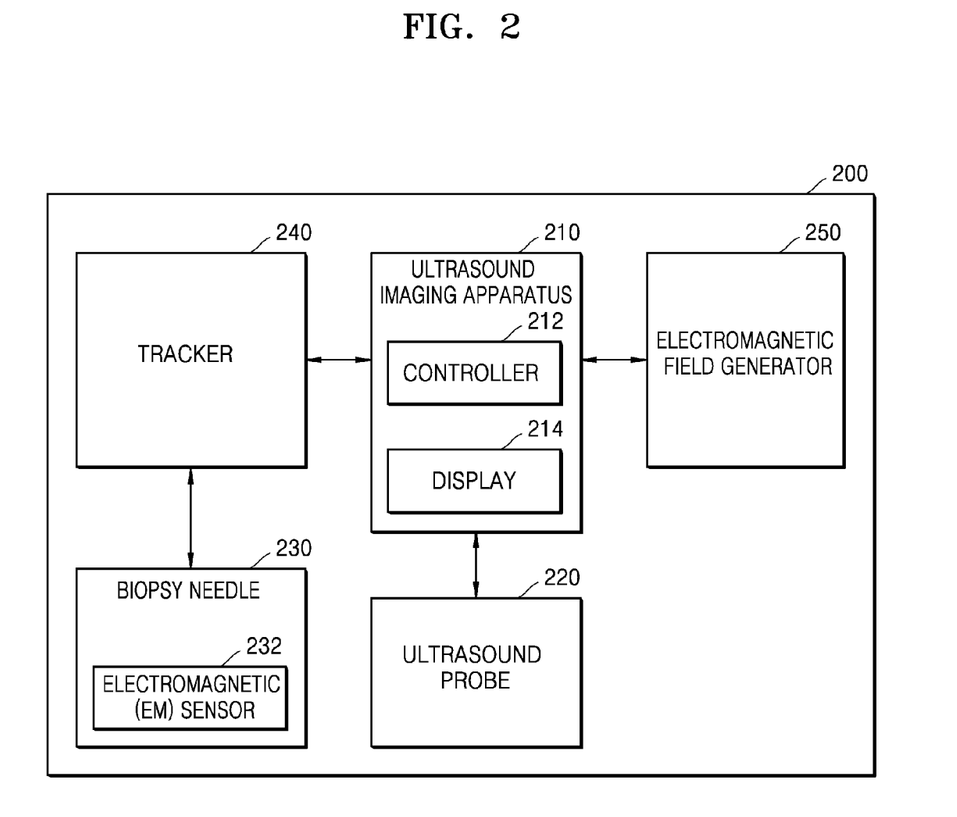
FIG. 2 is a block diagram illustrating a biopsy apparatus, according to an embodiment.

FIG. 2 is a block diagram illustrating a biopsy apparatus 200, according to an embodiment.

Referring to FIG. 2, the biopsy apparatus 200 may include an ultrasound imaging apparatus 210, an ultrasound probe 220, a biopsy needle 230, a tracker 240, and an electromagnetic field generator 250.

The ultrasound imaging apparatus 210 may receive an ultrasound echo signal from the ultrasound probe 220 and may perform image processing on the received ultrasound echo signal, in order to generate ultrasound images of a region inside an object. The ultrasound imaging apparatus 210 may be, but is not limited to, a cart-type apparatus.

For example, alternatively, the ultrasound imaging apparatus 210 may be a portable-type ultrasound imaging apparatus implemented by systems such as Picture Archiving and Communication System (PACS) viewers, smartphones, laptop computers, tablet personal computers (tablet PCs), personal digital assistants (PDAs), etc.

The ultrasound imaging apparatus 210 may include a controller 212 and a display 214. Although not illustrated in FIG. 2, the ultrasound imaging apparatus 210 may further include a user input unit to receive user input from the operator of the ultrasound imaging apparatus 210. The user input unit may be implemented as a button, a keypad, a mouse, a trackball, a touchscreen, etc. For example, the user input may select an operation mode of the ultrasound imaging apparatus 210. In the present embodiment, the ultrasound probe 220, the tracker 240, and the electromagnetic field generator 250 may be connected to the ultrasound imaging apparatus 210 via wires or may be connected wirelessly.

The controller 212 may control the operations of the ultrasound probe 220, the tracker 240, and the electromagnetic field generator 250, and manage the signal flow between components in the ultrasound imaging apparatus 210. In one embodiment, the controller 212 may be a hardware unit including a memory to store programs, algorithms, data, etc. for performing operations of the ultrasound imaging apparatus 210. The hardware unit may also include a processor to process the program, algorithms, and data stored in the memory. For example, the processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The controller 212 may determine an operation mode based on position and movement direction information of the biopsy needle 230 which is obtained from the tracker 240. Operation modes includes image registration mode where ultrasound images are properly registered with images of other modalities, and a biopsy mode. In the present embodiment, the memory of the controller 212 may store the algorithm for determining the operation mode using position coordinate values and the movement direction vector value of the biopsy needle 230. Further, the processor of the controller 212 may execute the algorithm to automatically switch between the image registration mode and the biopsy mode.

When the ultrasound imaging apparatus 210 includes a user input unit, the controller 212 may determine the operation mode based on the user input. For example, the user input may select the image registration mode or the biopsy mode.

The display 214 may display the ultrasound images generated by the ultrasound imaging apparatus 210. The display 214 may be implemented as a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a 3D display, a transparent display, etc. In the present embodiment, the display 214 may be a touchscreen.

The ultrasound probe 220 may include a transducer capable of transmitting ultrasound signals to the object and receiving ultrasound echo signals reflected from the object. In the present embodiment, the ultrasound probe 220 may be a probe that is separate from the ultrasound imaging apparatus 210 and is capable of independent operation.

The biopsy needle 230 may include an EM sensor 232. The electromagnetic field generator 250 may generate an electromagnetic field within a preset range from an area where the biopsy needle 230 to be inserted into the object is positioned The EM sensor 232 may detect the electromagnetic field generated by the electromagnetic field generator 250, and may provide position information as information in a 3D coordinates system to the tracker 240.

The tracker 240 may obtain 3D position coordinate values and the direction vector value of the biopsy needle 230 using the position information from the EM sensor 232. In more detail, the tracker 240 may obtain first coordinate values that are the initial 3D position coordinate values of the biopsy needle 230. And in the biopsy mode, when the biopsy needle 230 is inserted into the object and thus is moved, the biopsy needle 230 may obtain second coordinate values which are different from the initial 3D position coordinate values. The direction vector value of the biopsy needle 230 may be calculated from the first and second coordinate values.

Figure 3:
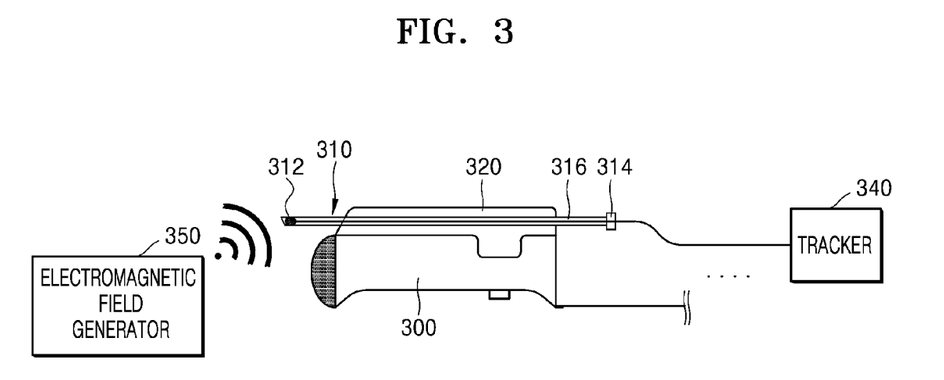
FIG. 3 is a diagram illustrating a configuration of the components of a biopsy apparatus, according to an embodiment.

FIG. 3 is a diagram illustrating a configuration of the components of a biopsy apparatus, according to an embodiment.

Referring to FIG. 3, the biopsy apparatus may include an ultrasound probe 300, a biopsy needle 310, a guide cover 320, a tracker 340, and an electromagnetic field generator 350. The ultrasound probe 300, the tracker 340, and the electromagnetic field generator 350 are respectively same components as the ultrasound probe 220, the tracker 240, and the electromagnetic field generator 250 described with reference to FIG. 2. Thus, redundant descriptions thereof are omitted here. For convenience of description, the biopsy needle 310 and the guide cover 320 in FIG. 3 are shown in cross section.

The biopsy needle 310 may include an EM sensor 312, a connecting member 314, and a connecting line 316.

The EM sensor 312 may be embedded into a first portion of the biopsy needle 310, i.e., an end of a body of the biopsy needle 310. The EM sensor 312 may detect the electromagnetic field generated by the electromagnetic field generator 350.

The connecting member 314 may cover an opening formed for the EM sensor 312 and the connecting line 316 in the biopsy needle 310. In the present embodiment, the connecting member 314 may be movable so that it can be opened or closed.

The connecting line 316 may electrically and/or physically connect the EM sensor 312 with the tracker 340. In the present embodiment, while in the electromagnetic field generated by the electromagnetic field generator 350, the EM sensor 312 may generate 3D position coordinate values. The EM sensor 312 may then transmit the 3D position coordinate values to the tracker 340 via the connecting line 316. Alternatively, the EM sensor 312 and the tracker 340 may be wirelessly connected to each other.

The guide cover 320 may be attached to one side of the ultrasound probe 300. The guide cover 320 may envelope the biopsy needle 310 to house the biopsy needle 310. The biopsy needle 310 may be extend from the guide cover 320 towards the object or retract into the guide cover 320. In the present embodiment, the biopsy needle 310 may extend from the guide cover 320 in the biopsy mode and may retract into the guide cover 320 in the image registration mode.

Figure 4:
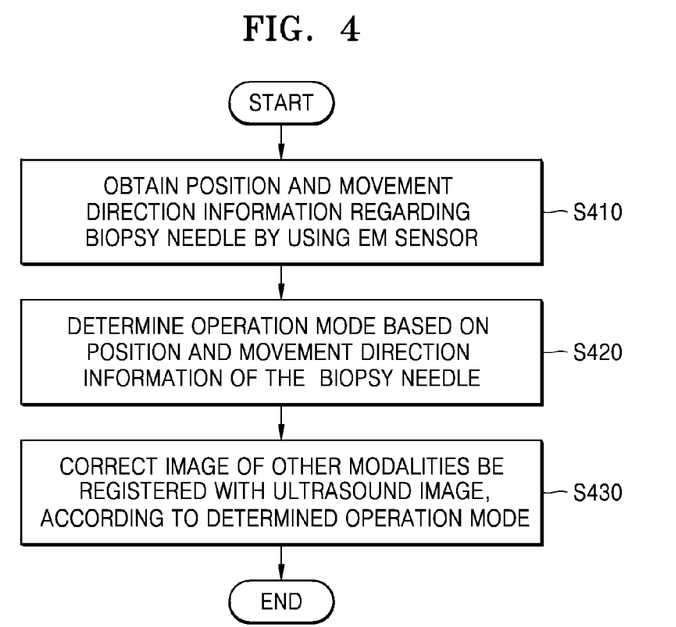
FIG. 4 is a flowchart illustrating a method of operating a biopsy apparatus, according to an embodiment.

FIG. 4 is a flowchart illustrating a method of operating a biopsy apparatus, according to an embodiment.

In operation S410, the biopsy apparatus obtains position and movement direction information of the biopsy needle using the EM sensor of the biopsy needle. In the present embodiment, the EM sensor of the biopsy needle may detect an electromagnetic field generated by an electromagnetic field generator, and may obtain first 3D position coordinate values of an initial position of the biopsy needle. The first position coordinate values may be coordinate values of the EM sensor in a 3D coordinates system. The biopsy apparatus may store the obtained first position coordinate values in a memory.

When the biopsy needle is inserted into the object to obtain a biopsy, the EM sensor in the biopsy needle may detect changes in the electromagnetic field, and may obtain second 3D position coordinate values corresponding to the changed position of the biopsy needle. In the present embodiment, using the first and second 3D position coordinate values, the biopsy apparatus may calculate a direction vector value for the biopsy needle. The biopsy apparatus may store the second position coordinate values and the direction vector value in the memory.

In operation S420, the biopsy apparatus determines the operation mode based on the position and movement direction information of the biopsy needle. The operation modes of the biopsy apparatus may include a biopsy mode in which the biopsy needle is moved into the object to obtain biopsies, and an image registration mode in which ultrasound images and image of other modalities are registered with each other. Images of other modalities may refer to medical images obtained using methods other than ultrasound. For example, image of other modalities may include CT images, MRI images, X-ray images, etc.

As explained above, the biopsy apparatus may calculate the position value and direction vector value of the biopsy needle, based on the difference between the second position coordinate values and the first position coordinate values which are obtained in operation S410. The biopsy apparatus may perform an algorithm of determining an operation mode by using the calculated position value and direction vector value of the biopsy needle. Detailed descriptions about the algorithm will be provided in detail with reference to FIG. 6.

In operation S430, the biopsy apparatus corrects the images of other modalities to be registered with the ultrasound image, according to the determined operation mode. When the biopsy apparatus is in the biopsy mode, the ultrasound probe is fixed at a specific position on the object and the biopsy needle is inserted into the object. Images of other modalities, e.g., an MRI image, may be obtained by a separate MRI apparatus. The MRI apparatus may be capturing MRI images according to the location and/or movement of the biopsy needle. This causes the ultrasound image and the MRI image to show different parts of the object, because the ultrasound probe has remained stationary while the biopsy needle has moved. In this case, registration between the ultrasound image and the MRI image is not appropriately achieved. In order for the ultrasound image and the MRI image to simultaneously display images of the same region, the correction in operation S430 may be performed by stopping the MRI apparatus prior to extending the biopsy needle into the object so that the MRI apparatus and the ultrasound probe captures images of the same region of the object.

Due to the correction performed in operation S430, registration accuracy between the ultrasound image and the images of other modalities may be increased.

Figure 5A:
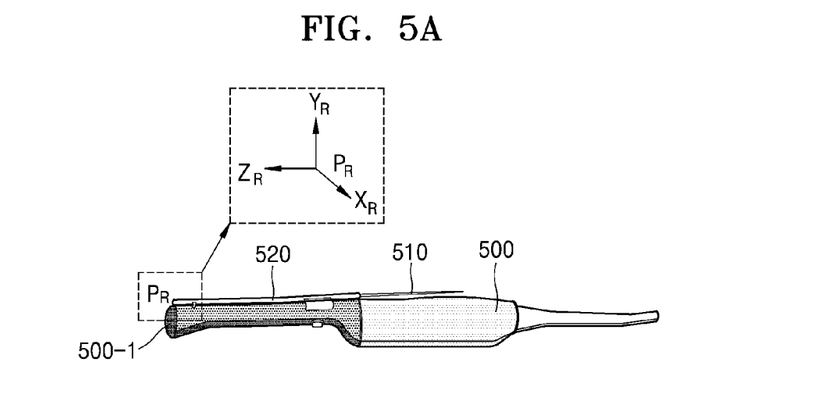
FIG. 5A and FIG. 5B are diagrams illustrating a method of obtaining position and movement direction information based on a movement of a biopsy needle attached to an ultrasound probe, according to an embodiment.
Figure 5B:
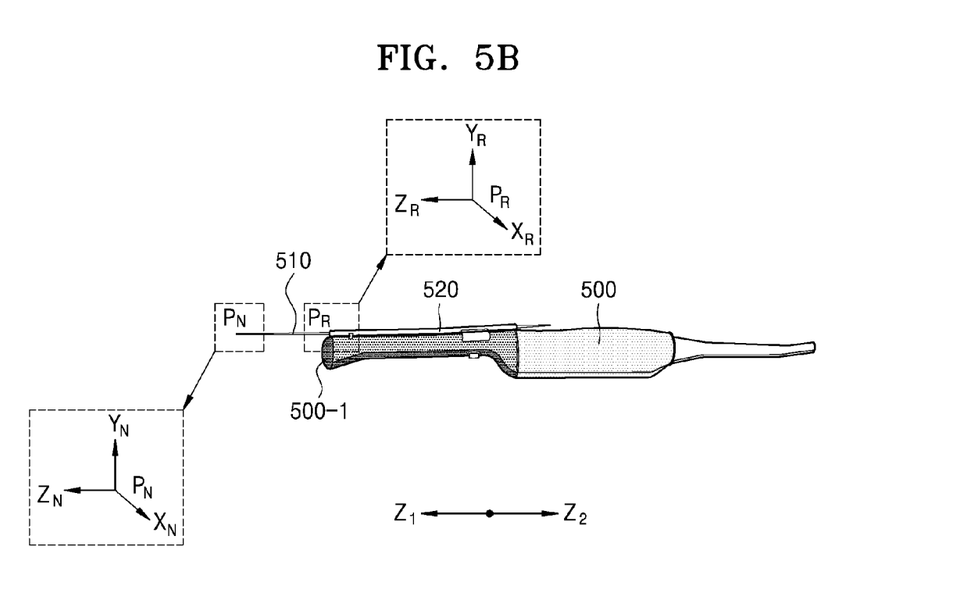

FIGS. 5A and 5B are diagrams illustrating a method of obtaining position and movement direction information based on a movement of a biopsy needle 510 attached to an ultrasound probe 500, according to an embodiment.

Referring to FIG. 5A, a guide cover 520 may be attached to one side of the ultrasound probe 500, and a biopsy needle 510 may be 1 enveloped by the guide cover 520.

An EM sensor embedded in the biopsy needle 510 may detect the electromagnetic field generated by an electromagnetic field generator and generate position information based on the electromagnetic field. The position information may be transmitted to a tracker, and the tracker may generate 3D position coordinate values $X_R$, $Y_R$, and $Z_R$ of the first position $P_R$ of the EM sensor. The 3D position coordinate values $X_R$, $Y_R$, and $Z_R$ may be the initial position or the starting point of the biopsy needle 510.

Referring to FIG. 5A, the first position $P_R$ may also reflect the location of the ultrasound probe 500. For example, first position $P_R$ may also be the position of a first end 500-1 of the ultrasound probe 500. In other words, the first position $P_R$ may refer to a position of the biopsy needle 510 when it is retracted in the guide cover 520, and the 3D position coordinate values $X_R$, $Y_R$, and $Z_R$ of the first position $P_R$ may be equal to 3D position coordinate values of the first end 500-1 of the ultrasound probe 500. In the present embodiment, the biopsy apparatus may set the 3D position coordinate values $X_R$, $Y_R$, and $Z_R$ of the first position $P_R$ as a reference value and may store them in a memory.

FIG. 5B illustrates an instance where an operator of the biopsy apparatus (e.g., a doctor) pushes the biopsy needle 510 to extend the biopsy needle 510 into the object.

Referring to FIG. 5B, the biopsy needle 510 may move to extend from the guide cover 520. After the movement, the EM sensor is now located at a second position $P_N$. The second position $P_N$ may be different from the first position $P_R$. In other words, when the operator moves the biopsy needle 510 to obtain a biopsy, 3D position coordinate values $X_N$, $Y_N$, and $Z_N$ of the second position $P_N$ may be different from the 3D position coordinate values $X_R$, $Y_R$, and $Z_R$ of the first position $P_R$ in FIG. 5A. The biopsy apparatus may store the 3D position coordinate values $X_N$, $Y_N$, and $Z_N$ of the second position $P_N$ in the memory.

The biopsy needle 510 may be moved in a first direction $Z_1$ and a second direction $Z_2$ in the guide cover 520, based on operator manipulation. For example, the first direction $Z_1$ may refer to the direction in which the biopsy needle 510 extends from the guide cover 520 and is inserted into the object. The second direction $Z_2$ may refer to the direction in which the biopsy needle 510 retracts into the guide cover 520 and is withdrawn from the object.

The biopsy apparatus may recognize whether or not the biopsy needle 510 is moved, by determining that the second position $P_N$ and the first position $P_R$ have different position coordinate values. In addition, the biopsy apparatus may obtain a movement direction vector value of the biopsy needle 510 using the difference between the second position $P_N$ and the first position $P_R$.

In the present embodiment, the biopsy apparatus may determine the operation mode by (1) calculating the difference in value between the first position $P_R$ of the biopsy needle 510 and the moved second position $P_N$ and (2) calculating a dot-product between the direction vector value $\vec{Z}_R$ at the first position $P_R$ and the direction vector value at the moved second position $P_N$. The biopsy apparatus may perform registration correction between ultrasound images and images of other modalities in the appropriate mode.

Figure 6:
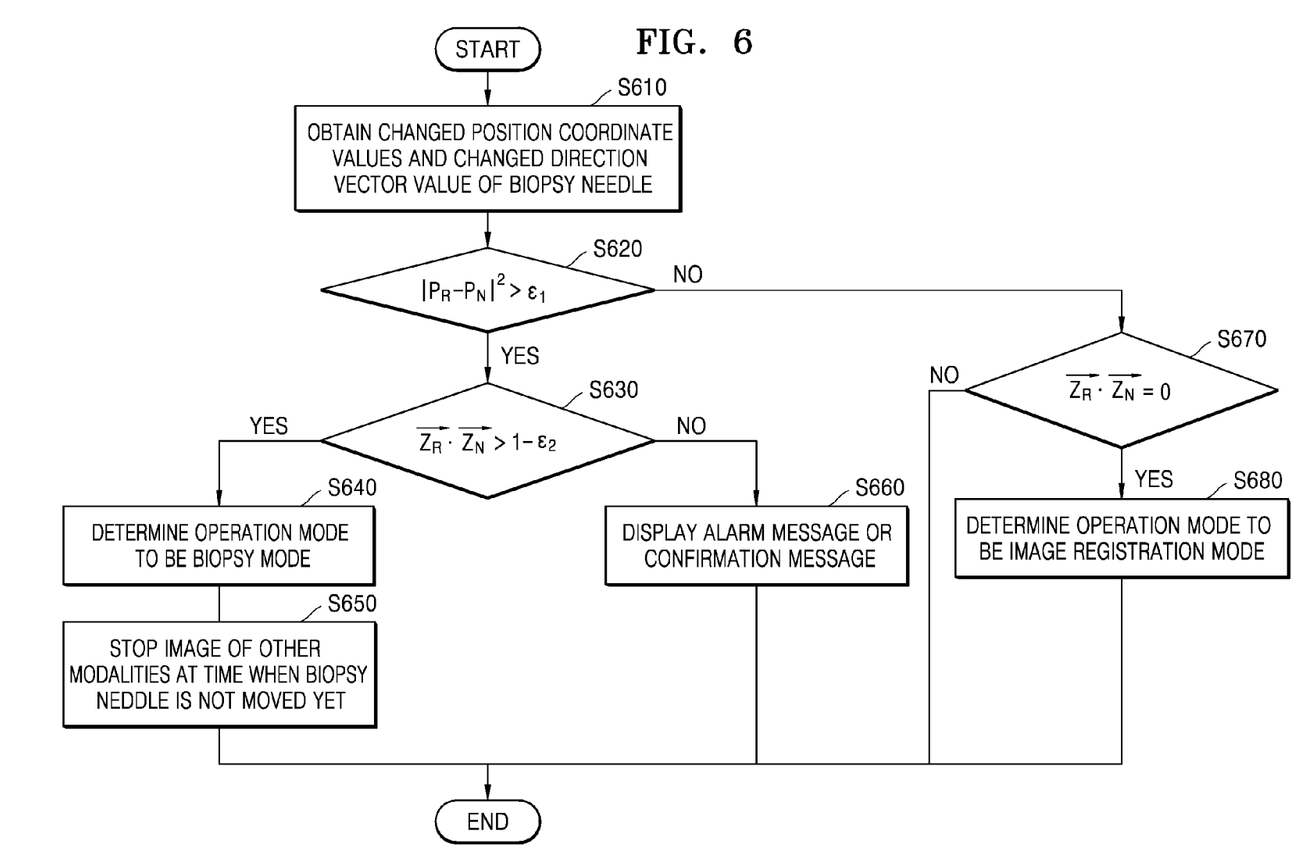
FIG. 6 is a flowchart illustrating a method, performed by a biopsy apparatus, of determining an operation mode, registering images, and performing correction, based on a position and a movement direction of a biopsy needle, according to an embodiment.

Detailed descriptions related to the method of determining the operation mode and correcting for image registration will be provided in detail with reference to FIG. 6.

FIG. 6 is a flowchart illustrating a method, performed by a biopsy apparatus, of determining an operation mode, registering images, and performing correction, based on a position and movement direction of a biopsy needle, according to an embodiment.

In operation S610, the biopsy apparatus obtains changed position coordinate values and a changed direction vector value of the biopsy needle. An EM sensor embedded in the biopsy needle may detect the electromagnetic field generated by an electromagnetic field generator and may transmit 3D position coordinate values generated based on the electromagnetic field to the biopsy apparatus. Referring to FIGS. 5A and 5B along with FIG. 6, the biopsy apparatus may obtain the 3D position coordinate values $X_R$, $Y_R$, and $Z_R$ of the first position $P_R$ of the biopsy needle 510 and the 3D position coordinate values $X_N$, $Y_N$, and $Z_N$ of the second position $P_N$ of the biopsy needle 510 when the biopsy needle 510 is moved by the operator (e.g., a doctor) to obtain a biopsy. The biopsy apparatus may also obtain the direction vector $\vec{Z_R}$ at the first position $P_R$ and the direction vector $\vec{Z_N}$ that correspond to the direction of the biopsy needle 510's movement. The direction vector $\vec{Z_N}$ may indicate movements in the first direction $Z_1$ or the second direction $Z_2$.

In operation S620, the biopsy apparatus may recognize whether or not the biopsy needle has moved. Referring to FIGS. 5A and 5B along with FIG. 6, the biopsy apparatus may calculate a distance between the 3D position coordinate values $X_R$, $Y_R$, and $Z_R$ of the first position $P_R$ and the 3D position coordinate values $X_N$, $Y_N$, and $Z_N$ of the second position $P_N$. The biopsy apparatus may determine whether the biopsy needle 510 has been moved by using Inequality 1 below.

$$|P_R - P_N|^2 > \varepsilon 1 \quad \text{[Inequality 1]}$$

where, $|P_R - P_N|$ may be the Euclidean distance between the first position $P_R$ and the second position $P_N$. In Inequality 1, the value of $\varepsilon 1$ may be a random positive number that is greater than 0 but is close to 0. If Inequality 1 indicates True, i.e., if the square of the Euclidean distance between the first position $P_R$ and the second position $P_N$ is greater than $\varepsilon 1$, the biopsy apparatus may determine that the biopsy needle has been moved. On the other hand, if Inequality 1 indicates False, the biopsy apparatus may determine that the biopsy needle is not moved.

When the biopsy apparatus determines that the biopsy needle has been moved (YES in operation S620), in operation S630, the biopsy apparatus determines whether the movement direction of the biopsy needle is equal to the direction of the ultrasound probe. For example, the direction of the ultrasound probe may be the direction vector $\vec{Z_R}$ at the first position $P_R$ and the movement direction of the biopsy needle may be the direction vector $\vec{Z_N}$ of the second position $P_N$ of the biopsy needle which are obtained in operation S610. In the present embodiment, the biopsy apparatus may recognize the movement direction of the biopsy needle by using Inequality 2 below.

$$\vec{Z_R} \cdot \vec{Z_N} > 1 - \varepsilon_2 \quad \text{[Inequality 2]}$$

In Inequality 2, a value of $\varepsilon 2$ may be a predetermined positive number that is greater than 0 but is close to 0. If Inequality 2 indicates True, i.e., if the dot-product between the direction vector $\vec{Z_R}$ at the first position $P_R$ and the direction vector $\vec{Z_N}$ of the second position $P_N$ is greater than $(1-\varepsilon_2)$, it may mean that the biopsy needle is being inserted into the object. Because the biopsy needle can move only in the first direction or the second direction that is opposite to the first direction in the guide cover, when the dot-product between the direction vector $\vec{Z_R}$ and the direction vector $\vec{Z_N}$ is greater than $(1-\varepsilon_2)$, the biopsy apparatus may recognize that the movement direction of the biopsy needle indicates a direction in which the biopsy needle is being inserted into the object. On the other hand, if Inequality 2 indicates False, i.e., if the dot-product between the direction vector $\vec{Z_R}$ at the first position $P_R$ and the direction vector $\vec{Z_N}$ of the second position $P_N$ is less than than $(1-\varepsilon_2)$, the biopsy apparatus may recognize that the biopsy needle is being retracted into the guide cover.

In operation S640, if the operation S630 results in YES, the biopsy apparatus may determine the operation mode to be the biopsy mode. In the biopsy mode, the biopsy needle may be inserted into the object. That is, if both Inequality 1 in operation S620 and Inequality 2 in operation S630 indicate True, the biopsy apparatus may recognize that the biopsy needle is moved by the operator (e.g. a doctor) to extend into the object. Accordingly, the biopsy apparatus may determine the operation mode to be the biopsy mode.

In operation S650, the biopsy apparatus performs correction on the images of other modalities the images of other modalities are paused at a point in time immediately prior to when the biopsy needle starts moving. When the operation mode is determined to be the biopsy mode, the biopsy apparatus may display the images of other modalities that are registered with the ultrasound images. When the biopsy needle is inserted into the object, the ultrasound probe stops moving. However, apparatus of other modalities, such as the CT apparatus or the MRI apparatus, may continue to move to follow the movement of the biopsy needle. In this case, the ultrasound imaging apparatus and the apparatuses of other modalities may be obtaining images from different areas of the object. To remedy this, the biopsy apparatus may pause the movement of the apparatuses so that still images at the first position $P_R$ are obtained by both the ultrasound imaging apparatus and the apparatuses of other modalities.

In operation S660, if the operation S630 results in NO, the biopsy apparatus displays an alarm message or a confirmation message on a display. When the biopsy apparatus determines that Inequality 1 indicates True in operation S620 and Inequality 2 indicates False in operation S630, i.e., when the biopsy needle is determined to have been moved but the movement direction is not towards the object, the biopsy apparatus may determine that the movement of the biopsy needle is wrong. The biopsy apparatus may output an error message or the alarm message to the display. In addition, the biopsy apparatus may output to the display a confirmation message asking the operator to check the movement direction of the biopsy needle.

In operation S670, if the operation S620 results in NO, the biopsy apparatus determines whether the dot-product between the direction vector $\vec{Z_R}$ at the first position $P_R$ and the direction vector $\vec{Z_N}$ of the second position $P_N$ is 0. If so, the biopsy apparatus may determine that the operator did not move the biopsy needle.

In operation S680, if operation S670 results in YES, the biopsy apparatus determines the operation mode to be the image registration mode.

In the present embodiment, if operation S670 results in NO, the biopsy apparatus may determine that the biopsy needle may be bent or deformed in the guide cover. In this case, the biopsy apparatus may cease operation.

Figure 7:
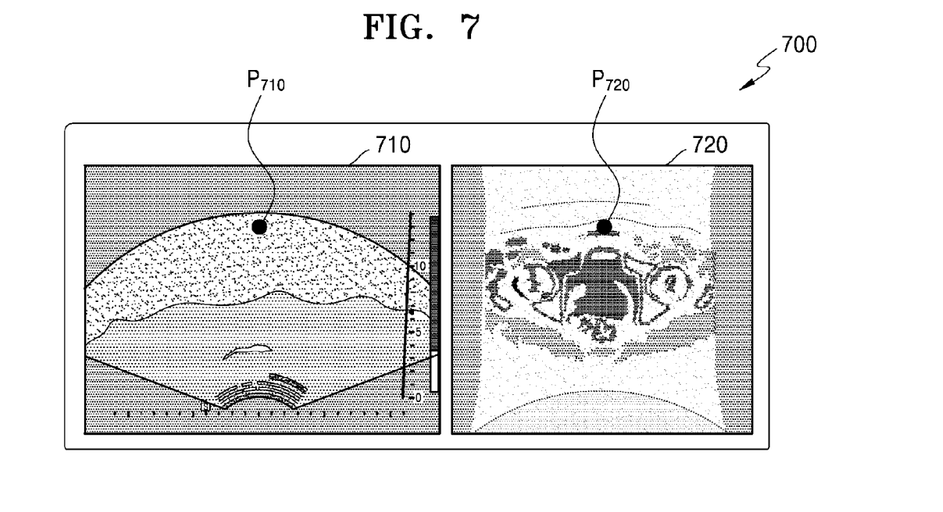
FIG. 7 is a diagram illustrating image registration between an ultrasound image and an image of another modality, according to an embodiment.

FIG. 7 is a diagram illustrating image registration between an ultrasound image and an image of another modality, according to an embodiment.

Referring to FIG. 7, the display 700 of the biopsy apparatus may display both an ultrasound image 710 and an image of another modality 720. The image 720 may refer to, but is not limited to, a CT image, an MRI image, an X-ray image, etc. The image 720 may refer to a medical diagnostic image that is not an ultrasound image.

While in the image registration mode, the biopsy apparatus may perform registration between the ultrasound image 710 and the image 720.

The biopsy apparatus may perform point-to-point registration where specific regions of the object are matched in both the ultrasound image 710 and the image of another modality 720. For example, as shown in FIG. 7, a first point $P_{710}$ displayed on the ultrasound image 710 may correspond to a specific region of the object. That region may also be shown in the image of another modality 720 at second point $P_{720}$. The point-to-point registration is well-known in the art to one of ordinary skill. Thus, detailed descriptions thereof are omitted here.

While FIG. 7 illustrates only the point-to-point registration, the image registration performed by the biopsy apparatus is not limited to the point-to-point registration. The biopsy apparatus may perform the image registration between the ultrasound image 710 and the image 720 by using all known image registration methods in the art.

Accordingly, as disclosed above, when a biopsy needle is inserted into the object, the biopsy apparatus may perform correction on the image of another modality 720 so that the image 720 is paused at a point in time immediately prior to when the biopsy needle starts moving. This is advantageous because in a biopsy mode, the operator of the biopsy apparatus (e.g., a doctor) may move the biopsy needle into the object. When this happens, the ultrasound probe may not move, but the apparatus of the other modality (e.g. a CT apparatus) may continue to move to follow the biopsy needle. In order to solve the mismatch between the ultrasound image and the images of other modalities, the biopsy apparatus may pause the image 720 at a point in time immediately prior to when the biopsy needle starts moving.

Figure 8:
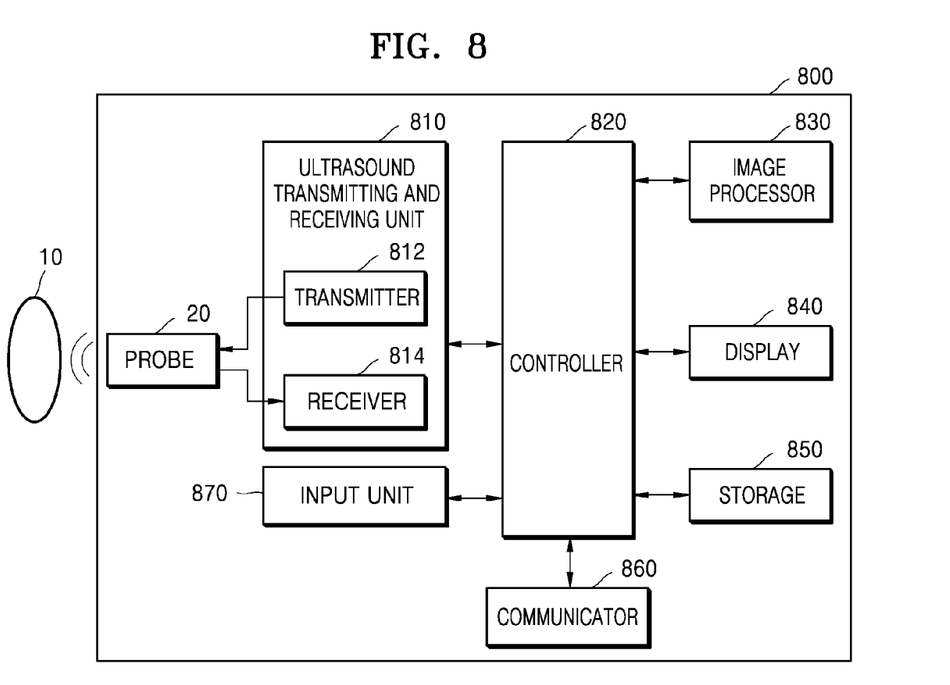
FIG. 8 is a block diagram illustrating an ultrasound imaging apparatus included in a biopsy apparatus, according to an embodiment.

FIG. 8 is a block diagram illustrating an ultrasound imaging apparatus 800 included in a biopsy apparatus, according to an embodiment. The ultrasound imaging apparatus 800 may include a probe 20, an ultrasound transmitting and receiving unit 810, a controller 820, an image processor 830, a display 840, a storage 850, a communicator 860, and an input unit 870.

The ultrasound imaging apparatus 800 may be a cart-type ultrasound imaging apparatus or a portable-type ultrasound imaging apparatus. Examples of the portable-type ultrasound imaging apparatuses may include systems implemented with smartphones, laptop computers, personal digital assistants (PDAs), and tablet personal computers (PCs), each of which may include a probe and a software application.

The probe 20 may include a plurality of transducers. The plurality of transducers may transmit ultrasound signals to the object 10 in response to transmission signals from the transmitter 812. The plurality of transducers may receive ultrasound echo signals reflected from the object 10 and generate reception signals from the received echo signals. The probe 20 and the ultrasound imaging apparatus 800 integrated into one body, or the probe 20 may be a separate probe that is connected to the ultrasound imaging apparatus 800 via a wire or wirelessly. The ultrasound imaging apparatus 800 may include the probe 20 or a plurality of the probes 20.

The controller 820 controls the transmitter 812 to generate the transmission signals to be transmitted to the plurality of transducers. The transmission signals may take into account the positions and focal points of the plurality of transducers in the probe 20.

The controller 820 controls the receiver 814, which may perform analog-to-digital conversion of the reception signals from the probe 20, and then to generate ultrasound data.

The image processor 830 generates ultrasound images by using the ultrasound data generated by the receiver 814.

The display 840 may display the generated ultrasound images and various types of information processed by the ultrasound imaging apparatus 800. According to various embodiments, the ultrasound imaging apparatus 800 may include the display 840 or a plurality of the displays 840. The display 840 may be combined with a touch panel so that it is a touchscreen.

The controller 820 may control the operations of the ultrasound imaging apparatus 800, and manage the signal flow between components in the ultrasound imaging apparatus 800. The controller 820 may include a memory to store programs or data for the operations of the ultrasound imaging apparatus 800, and a processor to process the programs or the data. In addition, the controller 820 may receive a control signal from the input unit 870, so that the operator of the ultrasound imaging apparatus 800 may control the ultrasound imaging apparatus 800 via the input unit 870.

The ultrasound imaging apparatus 800 may include the communicator 860 and may be in communication with an external apparatus (e.g., servers, medical apparatuses, portable devices (smartphones, tablet PCs, wearable devices, etc.), or the like) via the communicator 860.

The communicator 860 may include a component for communication with the external apparatus. For example, the communicator 860 may include a short-range communication module, a wired communication module, a wireless communication module, etc.

The communicator 860 may receive a control signal and data from the external apparatus and may deliver the received control signal to the controller 820, such that the controller 820 may control the ultrasound imaging apparatus 800 in response to the received control signal.

Alternatively, the controller 820 may transmit a control signal to the external apparatus via the communicator 860, such that the external apparatus may be controlled in response to the control signal of the controller 820.

For example, the external apparatus may process data in response to a control signal transmitted from the controller 820 via the communicator 860.

Programs for controlling the ultrasound imaging apparatus 800 may be installed in the external apparatus. These programs may include instructions for performing some or all operations of the controller 820.

The programs may be preinstalled on the external apparatus, or the user of the external apparatus may download the programs from servers. The servers may include a recording medium having the program recorded thereon.

The storage 850 may store various types of data or programs for driving and controlling the ultrasound imaging apparatus 800, such as ultrasound data, obtained ultrasound images, or the like.

The input unit 870 may receive a user input of controlling the ultrasound imaging apparatus 800. For example, the user input may include inputs generated by the manipulation of buttons, keypads, mice, trackballs, jog switches, knobs, touch inputs, voice inputs, motion inputs, bio-information inputs (for example, iris recognition or fingerprint recognition), etc.

Examples of the ultrasound imaging apparatus 800 are described below with reference to FIGS. 9A, 9B, and 9C.

Figure 9A:
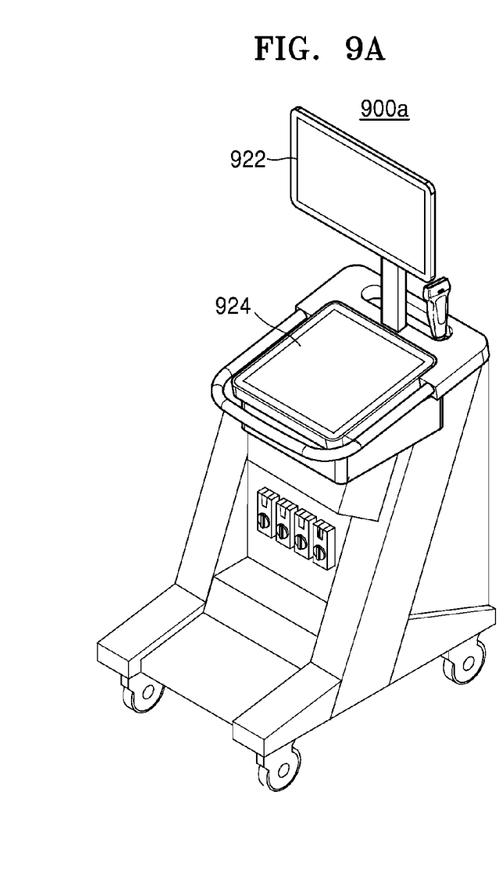
FIG. 9A, FIG. 9B, and FIG. 9C illustrate ultrasound imaging apparatuses according to three embodiments.
Figure 9B:
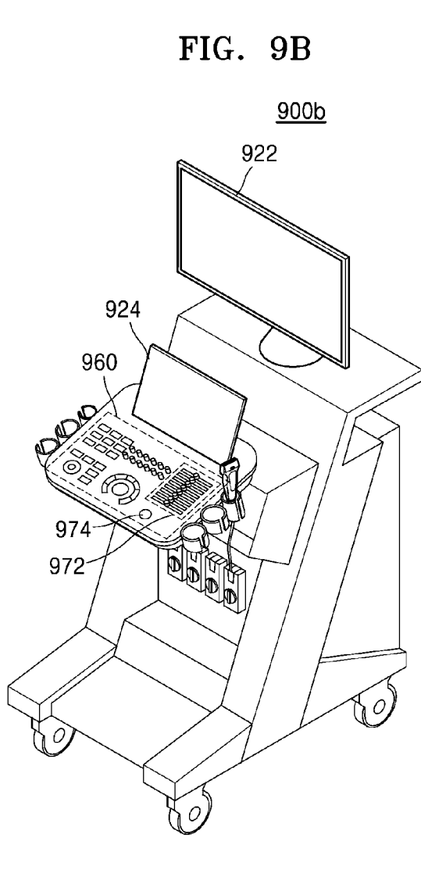
Figure 9C:
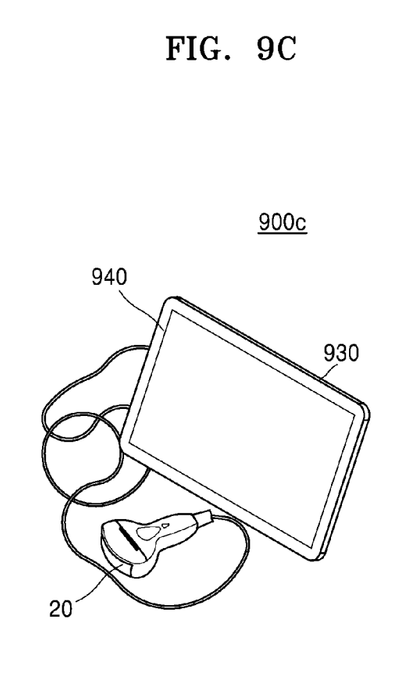

FIGS. 9A, 9B, and 9C illustrate ultrasound imaging apparatuses 900a, 900b, and 900c, each including a biopsy apparatus.

Referring to FIGS. 9A, 9B, and 9C, the ultrasound imaging apparatuses 900a and 900b may each include a main display 922 and a sub-display 924. One of the main display 922 and the sub-display 924 may be a touchscreen. The main display 922 and the sub-display 924 may display ultrasound images or various types of information processed by the ultrasound imaging apparatuses 900a and 900b. Alternatively, the main display 922 and the sub-display 924, when implemented as touchscreens, may provide graphical user interfaces (GUI) that allows the operator to enter inputs for controlling the ultrasound imaging apparatuses 900a and 900b. For example, the main display 922 may display ultrasound images, and the sub-display 924 may display a GUI control panel for controlling the ultrasound image.

Referring to FIG. 9B, the ultrasound imaging apparatus 900b may further include a physical control panel 960 in addition to the main display 922 and the sub-display 924. The control panel 960 may include buttons, trackballs, jog switches, knobs, or the like, and may receive user input from the operator for controlling the ultrasound imaging apparatus 900b. For example, the control panel 960 may include a time gain compensation (TGC) button 972, a freeze button 974, or the like. The TGC button 972 is a button for setting TGC values for adjusting the depths of ultrasound images. The freeze button 974 allows the operator to pause the currently displayed ultrasound image.

Alternatively, the buttons, the trackballs, the jog switches, the knobs, or the like included in the control panel 960 may be provided as software user interface elements in a GUI displayed on the main display 922 or the sub-display 924.

Referring to FIG. 9C, the ultrasound imaging apparatus 900c may be implemented as a portable-type ultrasound imaging apparatus 900c.

The ultrasound imaging apparatus 900c may include a probe 20 and a body 930, and the probe 20 may be connected to one side of the body 930 via a wire. Alternatively, the probe 20 may be connected to the body 930 wirelessly. The body 930 may include a touchscreen 940. The touchscreen 940 may display ultrasound images, various types of information processed by the ultrasound imaging apparatus 900c, GUIs, or the like.

Embodiments may be implemented through non-transitory computer-readable recording media having recorded thereon computer-executable instructions and data. The instructions may be program codes, and when the instructions are executed by a processor, the instructions may generate a preset program module to perform preset operations. Furthermore, when the instructions are executed by the processor, the instructions may perform specific operations according to the embodiments.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the present disclosure has been shown and described with reference to various embodiments thereof, it will be understood by those skilled in the art that various changes in form and details may be made therein without departing from the present disclosure as defined by the appended claims and their equivalents.

What is claimed is:

1. A biopsy apparatus comprising:
   an ultrasound probe configured to transmit an ultrasound signal to an object and to receive an echo signal reflected from the object, to thereby obtain an ultrasound image;
   a biopsy needle located at a side of the ultrasound probe, and including an electromagnetic (EM) sensor;
   a display;
   a tracker configured to obtain position information of the biopsy needle, the position information comprising first position coordinate values that indicate a first position of the biopsy needle and second position coordinate values that indicate a second position after the biopsy needle is inserted into the object, and movement direction information of the biopsy needle; and
   a controller configured to:
      receive, from the tracker, the position and movement direction information of the biopsy needle,
      compare a positional difference between the first position coordinate values and the second position coordinate values with a predetermined first threshold,
      compare a directional difference between a first direction of a first direction vector at the first position and a second direction of a second direction vector at the second position with a predetermined second threshold, and
      automatically select an operation mode from among an image registration mode and a biopsy mode based on a result of the comparisons,
   wherein the operation mode is selected from among the image registration mode where image registration is performed between the ultrasound image and an image of another modality, and the biopsy mode where a biopsy is performed using the biopsy needle, and
   wherein the controller is further configured to:
      control the display to display the ultrasound image and the image of another modality,
      determine whether a position of the biopsy needle is changed based on the comparison of the positional difference, determine whether a movement direction of the biopsy needle is toward the object based on the comparison of the directional difference, select the image registration mode based on the position of the biopsy needle not being changed, select the biopsy mode based on the position of the biopsy needle being changed and the movement direction of the biopsy needle being toward the object, control the display to display an alarm message or a confirmation message based on the position of the biopsy needle being changed and the movement direction of the biopsy needle being opposite to the object, perform registration correction between the ultrasound image and the image of another modality based on the operation mode being selected as the image registration mode, and pause the image of another modality based on the operation mode being selected as the biopsy mode, so that the display displays the image of another modality which is displayed on the display when the biopsy needle is at the first position.

2. The biopsy apparatus of claim 1, further comprising a guide cover attached to the side of the ultrasound probe, wherein the biopsy needle is enveloped by the guide cover, and is movable in a direction toward the ultrasound probe and a direction opposite to the ultrasound probe.

3. The biopsy apparatus of claim 1, further comprising an electromagnetic field generator configured to generate an electromagnetic field, wherein the EM sensor is configured to detect the electromagnetic field generated by the electromagnetic field generator, and the tracker is further configured to obtain the first position coordinate values from the EM sensor prior to a movement by the biopsy needle into the object.

4. A method of operating a biopsy apparatus comprising an ultrasound probe and a biopsy needle attached to a side of the ultrasound probe and insertable into an object, the method comprising:

obtaining position information of the biopsy needle, the position information comprising first position coordinate values that indicate a first position of the biopsy needle and second position coordinate values that indicate a second position after the biopsy needle is inserted into the object, and movement direction information of the biopsy needle using an electromagnetic (EM) sensor included in the biopsy needle;

comparing a positional difference between the first position coordinate values and the second position coordinate values with a predetermined first threshold;

comparing a directional difference between a first direction of a first direction vector at the first position and a second direction of a second direction vector at the second position with a predetermined second threshold;

automatically selecting an operation mode from among an image registration mode and a biopsy mode based on a result of the comparisons, wherein the operation mode is selected from among the image registration mode where image registration is performed between an ultrasound image and an image of another modality, and the biopsy mode where a biopsy is performed using the biopsy needle;

displaying the ultrasound image and the image of another modality on a display; and correcting at least one of the ultrasound image or the image of another modality based on the operation mode, wherein the selecting of the operation mode comprises:
determining whether a position of the biopsy needle is changed based on the comparison of the positional difference, determining whether a movement direction of the biopsy needle is toward the object based on the comparison of the directional difference, selecting the image registration mode based on the position of the biopsy needle not being changed, selecting the biopsy mode based on the position of the biopsy needle being changed and the movement direction of the biopsy needled being toward the object, and displaying an alarm message or a confirmation message on the display based on the position of the biopsy needle being changed and the movement direction of the biopsy needle being opposite to the object, wherein the correcting of the at least one of the ultrasound image or the image of another modality comprises:
performing registration correction between the ultrasound image and the image of another modality based on the operation mode being selected as the image registration mode, and pausing the image of another modality based on the operation mode being selected as the biopsy mode, so that the display displays the image of another modality which is displayed on the display when the biopsy needle is at the first position.

5. The method of claim 4, wherein the obtaining of the position and movement direction information of the biopsy needle comprises:

obtaining the first position coordinate values prior to a movement by the biopsy needle into the object, by detecting an electromagnetic field generated by an electromagnetic field generator; and obtaining a direction vector value and the second position coordinate values after the movement by the biopsy needle into the object.

6. The method of claim 4, wherein the performing of the registration correction comprises performing image registration between the ultrasound image and the image of another modality using a point-to-point registration technique.

7. A non-transitory computer-readable recording medium having recorded thereon at least one program that, when executed by a processor, causes the processor to perform:

obtaining position information of the biopsy needle, the position information comprising first position coordinate values that indicate a first position of the biopsy needle and second position coordinate values that indicate a second position after the biopsy needle is inserted into the object, and movement direction information of the biopsy needle using an electromagnetic (EM) sensor included in the biopsy needle;

comparing a positional difference between the first position coordinate values and the second position coordinate values with a predetermined first threshold;

comparing a directional difference between a first direction of a first direction vector at the first position and a second direction of a second direction vector at the second position with a predetermined second threshold;

automatically selecting an operation mode from among an image registration mode and a biopsy mode based on a result of the comparisons, wherein the operation mode is selected from among the image registration mode where image registration is performed between an ultrasound image and an image of another modality, and the biopsy mode where a biopsy is performed using the biopsy needle;

causing a display to display the ultrasound image and the image of another modality; and correcting at least one of the ultrasound image or the image of another modality based on the operation mode, wherein the selecting of the operation mode comprises:
  determining whether a position of the biopsy needle is changed based on the comparison of the positional difference,
  determining whether a movement direction of the biopsy needle is toward the object based on the comparison of the directional difference,
  selecting the image registration mode based on the position of the biopsy needle not being changed,
  selecting the biopsy mode based on the position of the biopsy needle being changed and the movement direction of the biopsy needled being toward the object, and
  causing the display to an alarm message or a confirmation message, based on the position of the biopsy needle being changed and the movement direction of the biopsy needle being opposite to the object, wherein the correcting of the at least one of the ultrasound image or the image of another modality comprises:
  performing registration correction between the ultrasound image and the image of another modality based on the operation mode being selected as the image registration mode, and
  pausing the image of another modality based on the operation mode being selected as the biopsy mode, so as to cause the display to display the image of another modality which is displayed on the display when the biopsy needle is at the first position.

\* \* \* \* \*